United States Patent
Stewart et al.

(10) Patent No.: US 12,282,010 B2
(45) Date of Patent: Apr. 22, 2025

(54) AUTOMATED ANALYSIS OF DRILLING FLUID

(71) Applicant: Schlumberger Technology Corporation, Sugar Land, TX (US)

(72) Inventors: Colin Stewart, Houston, TX (US); Truls Fossdal, Sandsli (NO); Ragnar Melz, Sandnes (NO); Jerry Thomas Connaughton, Richmond, TX (US); Zakhar Chizhov, Katy, TX (US); Neil McPherson, Houston, TX (US); Rahul Sheladia, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 17/980,819

(22) Filed: Nov. 4, 2022

(65) Prior Publication Data

US 2023/0048482 A1  Feb. 16, 2023

Related U.S. Application Data

(63) Continuation of application No. 16/623,383, filed as application No. PCT/US2018/040769 on Jul. 3, 2018, now abandoned.
(Continued)

(51) Int. Cl.
*G01N 11/14* (2006.01)
*G01N 9/36* (2006.01)
(Continued)

(52) U.S. Cl.
CPC ........... *G01N 33/2823* (2013.01); *G01N 9/36* (2013.01); *G01N 11/14* (2013.01); *G01N 2011/0093* (2013.01)

(58) Field of Classification Search
None
See application file for complete search history.

(56) References Cited

U.S. PATENT DOCUMENTS

| | | |
|---|---|---|
| 4,086,061 A | 4/1978 | Hoffa et al. |
| 4,273,650 A | 6/1981 | Solomon |

(Continued)

FOREIGN PATENT DOCUMENTS

| | | |
|---|---|---|
| CN | 2783315 Y | 5/2006 |
| CN | 101842679 A | 9/2010 |

(Continued)

OTHER PUBLICATIONS

International Search Report and Written Opinion issued in International Patent Application No. PCT/US2020/045183 on Nov. 24, 2020, 13 pages.

(Continued)

*Primary Examiner* — Alexander A Mercado
(74) *Attorney, Agent, or Firm* — Cameron R. Sneddon; Jeffrey D. Frantz

(57) ABSTRACT

A system includes a fluid conduit, a fluid chamber in communication with the fluid conduit, a rheology sensor in communication with the fluid chamber, and an electric temperature controller in communication with the fluid chamber. The fluid chamber is cooled in response to a first control signal from the electric temperature controller.

20 Claims, 8 Drawing Sheets

Related U.S. Application Data

(60) Provisional application No. 62/529,454, filed on Jul. 6, 2017.

(51) Int. Cl.
  *G01N 33/28* (2006.01)
  *G01N 11/00* (2006.01)

(56) References Cited

U.S. PATENT DOCUMENTS

| | | | |
|---|---|---|---|
| 4,518,700 A * | 5/1985 | Stephens | G05D 23/1919 432/83 |
| 5,780,737 A | 7/1998 | Wible et al. | |
| 6,240,770 B1 | 6/2001 | Raffer | |
| 6,257,354 B1 | 7/2001 | Schrader et al. | |
| 6,330,826 B1 | 12/2001 | Meeten | |
| 6,584,833 B1 | 7/2003 | Jamison et al. | |
| 6,931,916 B2 | 8/2005 | Zamora et al. | |
| 8,387,442 B2 | 3/2013 | Jamison et al. | |
| 8,784,745 B2 | 7/2014 | Nelson et al. | |
| 8,881,577 B1 | 11/2014 | Agar et al. | |
| 9,134,291 B2 | 9/2015 | Jamison et al. | |
| 9,194,972 B2 | 11/2015 | Van Der Zwaag | |
| 9,222,351 B2 | 12/2015 | Jamison | |
| 9,428,976 B2 | 8/2016 | Porter et al. | |
| 9,513,203 B2 | 12/2016 | Kulkarni et al. | |
| 9,777,542 B2 | 10/2017 | Stock et al. | |
| 2003/0084708 A1 | 5/2003 | Abnett | |
| 2003/0233867 A1 | 12/2003 | Hall | |
| 2006/0175547 A1 | 8/2006 | DiFoggio et al. | |
| 2006/0243047 A1 | 11/2006 | Terabayashi et al. | |
| 2008/0066537 A1 | 3/2008 | Hegeman et al. | |
| 2009/0151426 A1 | 6/2009 | Shah | |
| 2010/0304418 A1 | 12/2010 | Moussavi et al. | |
| 2012/0094876 A1 | 4/2012 | Jamison et al. | |
| 2013/0009784 A1 | 1/2013 | Villard et al. | |
| 2013/0277113 A1 | 10/2013 | Murphy | |
| 2013/0312511 A1 * | 11/2013 | Jamison | G01N 15/04 73/152.05 |
| 2014/0096930 A1 | 4/2014 | Krug, Jr. | |
| 2014/0105446 A1 | 4/2014 | Maxey et al. | |
| 2014/0166361 A1 | 6/2014 | Jamison et al. | |
| 2014/0202772 A1 | 7/2014 | Kulkarni et al. | |
| 2014/0319080 A1 | 10/2014 | Kaarigstad et al. | |
| 2015/0233614 A1 | 8/2015 | Kindt et al. | |
| 2015/0316527 A1 | 11/2015 | Stock et al. | |
| 2016/0040533 A1 | 2/2016 | Harrison et al. | |
| 2016/0138395 A1 | 5/2016 | Kulkarni et al. | |
| 2016/0265029 A1 | 9/2016 | Ying et al. | |
| 2016/0313292 A1 | 10/2016 | Desai et al. | |
| 2016/0356919 A1 | 12/2016 | Jamison et al. | |
| 2017/0038491 A1 | 2/2017 | Gonzalez et al. | |
| 2017/0198189 A1 | 7/2017 | Panamarathupalayam | |
| 2018/0164201 A1 | 6/2018 | Zimmer et al. | |
| 2018/0266930 A1 | 9/2018 | Nowak et al. | |
| 2020/0124513 A1 | 4/2020 | Gao et al. | |
| 2020/0182852 A1 | 6/2020 | Stewart et al. | |
| 2021/0088499 A1 | 3/2021 | Stewart et al. | |
| 2023/0149867 A1 * | 5/2023 | Smith | B01F 35/2136 366/124 |

FOREIGN PATENT DOCUMENTS

| | | | |
|---|---|---|---|
| CN | 102187199 A | | 9/2011 |
| CN | 203025064 U | | 6/2013 |
| CN | 106092976 A | | 11/2016 |
| CN | 106415236 A | | 2/2017 |
| CN | 107780858 A | | 3/2018 |
| CN | 209109371 U | | 7/2019 |
| GB | 1379470 A | | 1/1975 |
| GB | 2344180 A | | 5/2000 |
| JP | H1078824 A | | 3/1998 |
| JP | 2003083859 A | | 3/2003 |
| JP | 2007086035 A | | 4/2007 |
| KR | 20110075086 A | | 7/2011 |
| WO | 0167068 A2 | | 9/2001 |
| WO | 2009079059 A1 | | 6/2009 |
| WO | 2011100435 A2 | | 8/2011 |
| WO | 2015191091 A1 | | 12/2015 |

OTHER PUBLICATIONS

International Preliminary Report on Patentability issued in International Patent Application No. PCT/US2020/045183 on Apr. 7, 2022, 10 pages.
Search Report and Written Opinion of International Patent Application No. PCT/US2018/040769 dated Oct. 25, 2018, 6 pages.
International Preliminary Report on Patentability issued in Intentional Patent Application No. PCT/US2018/040769 on Jan. 7, 2020, 5 pages.
Search and Examination report issued in European Patent Application 18827666.1 on Feb. 11, 2021, 14 pages.
Garma Electronica s.l., Advantages of Thermal Dispersion Level Switch, Retrieved from the internet: URL: https://www.https://www.garmasl.com/en/blog/82-advantages-of-thermal-dispersion-level-switch, Published Nov. 8, 2016, retrieved on Feb. 1, 2021, 2 pages.
Office Action issued in U.S. Appl. No. 16/578,570 dated Oct. 4, 2021, 18 pages.
API 13B-1 Standard, "Recommended Practice for Field Testing Water-based Drilling Fluids," Fourth Edition, Mar. 2009, Errata 1, Aug. 2014, 104 pages.
API 13B-2 Standard, "Recommended Practice for Field Testing Oil-based Drilling Fluids," Fifth Edition, Apr. 2014, Errata 1, Aug. 2014, 154 pages.
Fann Instrument Company, Model 35 Viscometer Instruction Manual, Houston, Texas, 2016, 45 pages.
English Translation of JP-H1078824-A (Year: 1998).
Office Action issued in U.S. Appl. No. 16/623,383 dated Dec. 27, 2021, 17 pages.
Search Report and Written Opinion of Russian Patent Application No. 2020104983 dated Jan. 21, 2022, 16 pages with English translation.
Exam Report issued in India Patent Application No. 202017001853 dated Feb. 28, 2022, 5 pages.
Saasen, et al., Prediction of Barite Sag Potential of Drilling Fluids From Rheological Measurements, Society of Petroleum Engineers, SPE-29410 (1995).
Office Action issued in U.S. Appl. No. 16/656,491 dated Mar. 10, 2022, 10 pages.
First Office Action issued in Chinese Patent Application No. 2018800443773 dated Apr. 26, 2022, 26 pages with English translation.
Office Action issued in U.S. Appl. No. 16/578,570 dated May 13, 2022, 18 pages.
Preliminary Office Action issued in Brazil Patent Application No. BR112019028218-1 dated Aug. 4, 2022, 6 pages with English translation.
Nagy, M. J. et al., "The Effect of Pulse Width Modulation (PWM) Frequency on the Reliability of Thermoelectric Modules", IEEE presented at the 18th International Conference on Thermoelectrics, Piscataway, New Jersey, U.S.A., 1999, pp. 123-125.
Communication Pursuant to Article 94(3) issued in European Patent Application No. 18827666.1 dated Aug. 22, 2022, 9 pages.
Notice of Allowance issued in U.S. Appl. No. 16/578,570 dated Sep. 7, 2022, 10 pages.
Decision on Grant issued in Russian Patent Application No. 2020104983 dated Sep. 22, 2022, 19 pages with English translation.
Office Action issued in Colombia Patent Application NC2020/0001163 dated Sep. 26, 2022, 28 pages with English translation.
Exam Report issued in Kuwait Patent Application No. KW/P/2019/433 dated May 16, 2022, 4 pages.
Second Office Action issued in Chinese Patent Application No. 2018800443773 dated Jan. 5, 2023, 25 pages with English translation.
Notice of Allowance issued in U.S. Appl. No. 16/587,570 dated Jan. 11, 2023, 13 pages.

(56) References Cited

OTHER PUBLICATIONS

Written Opinion issued in Brazilian patent application 1120190282181 on Feb. 7, 2023, 11 pages with English translation.
Exam Report under Section 18(3) issued in United Kingdom Patent Application No. GB2204086.9 dated Mar. 7, 2023, 4 pages.
Examination Report issued in Great Britian Patent Appl. No. GB2204086.9 on Oct. 6, 2023; 3 pages.
Office Action and Search Report issued in UAE Patent Application P6000023/2020 on Oct. 30, 2023, 9 pages.
2nd Exam Report issued in Saudi Arabia Patent Application No. 520410938 dated Oct. 12, 2023, 30 pages.
Office Action issued in Colombia Patent Application No. NC2020/0001163 dated Nov. 14, 2023, 32 pages with English translation.
Substantive Exam issued in Saudi Arabia Patent Application No. 520410938 dated Mar. 30, 2023, 29 pages.
First Office Action issued in Mexico Patent Application No. MX/a/2020/000181 dated Mar. 29, 2023, 10 pages.
Office Action issued in Colombia Patent Application NC2020/0001163 dated Apr. 27, 2023, 29 pages.
Exam Report No. 1 issued in Australia Patent Application No. 2018298054 dated Apr. 15, 2023, 3 pages.
Substantive Exam issued in Saudi Arabia Patent Application No. 522432037 dated May 18, 2023, 15 pages.
Decision of Rejection issued in China Patent Application No. 201880044377.3 dated May 26, 2023, 23 pages.
Substantive Exam issued in Bahrain Patent Application No. 20190305 dated Aug. 22, 2023, 10 pages.
Hearing Notice issued in India Patent Application No. 202017001853 dated Feb. 26, 2024, 6 pages.
Examination Report issued in Malaysian Patent Application PI2020000051 on Mar. 25, 2024, 4 pages.
2nd Substantive Exam issued in Bahrain Patent Application No. 20190305 dated Jul. 10, 2024, 11 pages with partial English translation.
First Office Action and Search Report issued in Chinese Patent Application No. 2020800715578 dated Sep. 2, 2024, 31 pages with English translation.
Exam Report issued in Canadian Patent Application No. 3068835 dated Nov. 4, 2024, 8 pages.

\* cited by examiner

AUTOMATED ANALYSIS OF DRILLING FLUID

CROSS-REFERENCE TO RELATED APPLICATIONS

This application is a continuation of U.S. patent application Ser. No. 16/623,383, with a filing date of Dec. 16, 2019, which is the national stage application, filed under 35 U.S.C. § 371, of International Patent Application No. PCT/US2018/040769, filed on, Jul. 3, 2018, which claims priority to U.S. Provisional Patent Application No. 62/529,454, filed on Jul. 6, 2017, the contents of which are incorporated by reference.

BACKGROUND

Drilling fluids are pumped the center of a down drill string when drilling a wellbore. The drilling fluid exits the drill string at the bit through nozzles and travels back up the annulus of the wellbore to the drilling equipment located at the surface. The fluids provide lubrication and cooling of the drilling. The fluid also carries cuttings out of the wellbore, controls wellbore pressure, and performs a number of other functions in connection with drilling the wellbore. To ensure that the properties of the drilling fluids are adequate, an engineer consistently checks the properties of the drilling fluid. For example, the viscosity of the drilling fluid must be high enough to carry the cuttings out of the wellbore while at the same time be low enough to allow the cuttings and entrained gas to escape the drilling fluids at the surface. Depending on the operation, the engineer may check the properties of the drilling fluid several times in a 24 hour period.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

Figure 1:
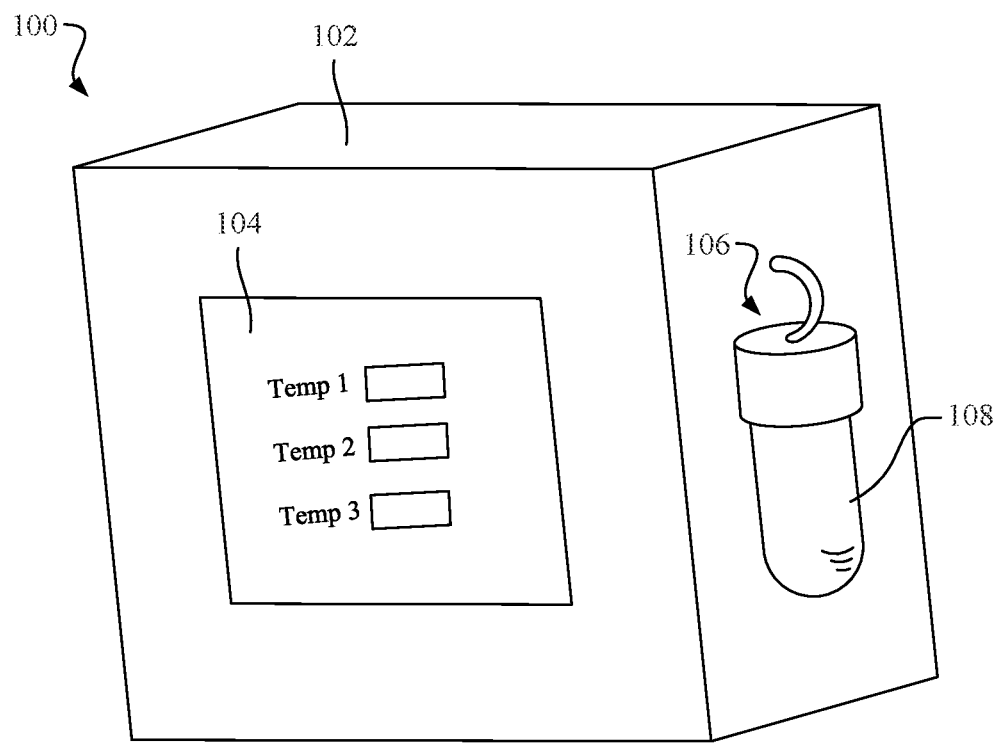
FIG. 1 depicts a perspective view of an example of fluid testing apparatus in accordance with the present disclosure.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Drilling fluid is circulated down the drill string, out the nozzles in the drill bit, and up the annulus of the wellbore. The drilling fluid can be used to remove cuttings from the bottom of the wellbore. The physical properties of the drilling mud are monitored during a drilling operation to determine whether the drilling mud is working adequately and to make any desired changes as drilling progresses.

The drilling fluid tests may measure physical characteristics of the drilling fluid, such as testing the fluid's rheology. Rheology tests may be performed with a rheology meter, such as a viscometer, a rheometer, or another type of sensor. These tests may be performed onsite at the wellbore, in a lab, or at another location. The fluid testing apparatus 100 depicted in FIG. 1 may complete a series of tests on the drilling fluid sequentially without further instructions from the user between tests. Other types of fluid property tests that may be performed with the fluid testing apparatus 100 include taking measurements of the mud weight, rheology, density, water-oil content, emulsion electrical stability, fluid conductivity, and particle size distribution. Based on the principles described in the present disclosure, a fluid testing apparatus 100 may perform at least one or more of the fluid property tests automatically at different temperatures.

The fluid testing apparatus 100 may include a housing 102, a user interface 104, and a bottle receiver 106. A drilling fluid sample may be collected from the circulating drilling mud or from another location into a bottle 108. The bottle 108 may be connect to the bottle receiver 106. A fluid conduit may be suspended from the bottle receiver 106 and be submerged into the drilling fluid sample as the bottle 108 is connected to the bottle receiver 106. A pump may actively convey at least a portion of the drilling fluid sample out of the bottle 108 into the fluid testing apparatus 100 where the tests may be performed.

The bottle 108 may be secured to the bottle receiver 106 through any appropriate type of interface. In some examples, the bottle receiver 106 has an internal thread that can be engaged with an external thread of the bottle 108. In other examples, the bottle 108 is snapped into place, held in place through compression, otherwise interlocked with the bottle receiver 106, or otherwise connected to the bottle receiver 106 though another type of attachment.

The user interface 104 may allow the user to instruct the fluid testing apparatus 100 to perform the tests. In some examples, the fluid testing apparatus 100 presents options for testing the drilling fluid sample through the user interface 104. In some cases, the user may indicate the types of tests to be performed as well as parameters for performing those types of tests. For example, the user may instruct the fluid testing apparatus 100 to perform a viscosity test at multiple temperatures through the user interface 104. The user may also specify the desired temperatures for those tests through the user interface 104.

Any type of user interface 104 may be used in accordance with the principles described in the present disclosure. In some cases, the user interface 104 is a touch screen accessible from the housing 102 of the fluid testing apparatus 100. In this type of example, the user may touch the touch screen to input information and provide instructions to the fluid testing apparatus 100. In other examples, the fluid testing apparatus 100 may include a wireless receiver where the user can provide information and/or send instructions wirelessly to the fluid testing apparatus 100. For example, the user may send the information and/or provide the instructions with a mobile device, an electric tablet, a laptop, a networked device, a desktop, a computing device, another type of device, or combinations thereof. In examples where the user can communicate with the fluid testing apparatus 100 wirelessly, the user may be located onsite or the user may be located at a remote location. In some cases, a mud engineer may be located at a remote location offsite and a local technician may fill the bottle 108 for the mud engineer so that the mud engineer does not have be onsite to evaluate the drilling mud and make recommendations. In yet another example, the user interface 104 may include a keyboard, a mouse, a button, a dial, a switch, a slider, another type of physical input mechanism, or combinations thereof to assist the user to input information or provide instructions to the fluid testing apparatus 100. In some cases, the fluid testing apparatus 100 may include a microphone or a camera that allows the user to speak information to the fluid testing apparatus 100 and/or communicate with motion/hand gestures with the fluid testing apparatus 100.

After inputting the information and instructing the fluid testing apparatus 100 to initiate the tests, the fluid testing apparatus 100 may complete the tests without further involvement from the user. The fluid testing apparatus 100 may automatically transition from one type of test to another as tests are completed. Further, the fluid testing apparatus 100 may automatically adjust the temperature of the drilling fluid sample between tests without involvement from the user. Often, the drilling mud is tested after circulating through the drill string in a hot, downhole environment. In those circumstances where the drilling mud is desired to be tested at a temperature lower than the current temperature of the drilling mud, the drilling mud has to be cooled off before the test can be performed. The fluid testing apparatus 100 may lower the drilling fluid sample's temperature and free the user to perform other tasks.

Figure 2:
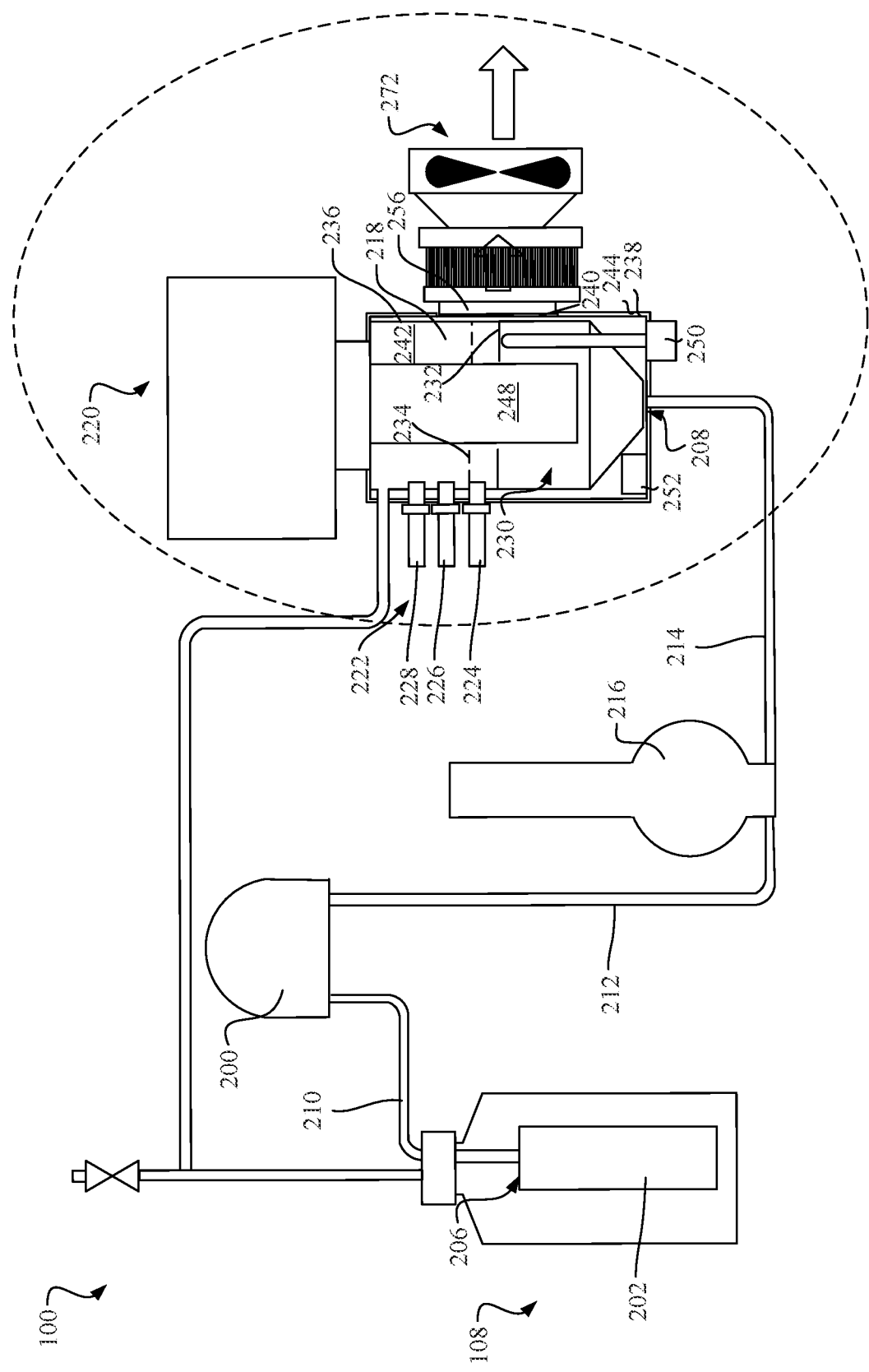
FIG. 2 depicts a schematic of an example of internal components of a fluid testing apparatus in accordance with the present disclosure.
Figure 3:
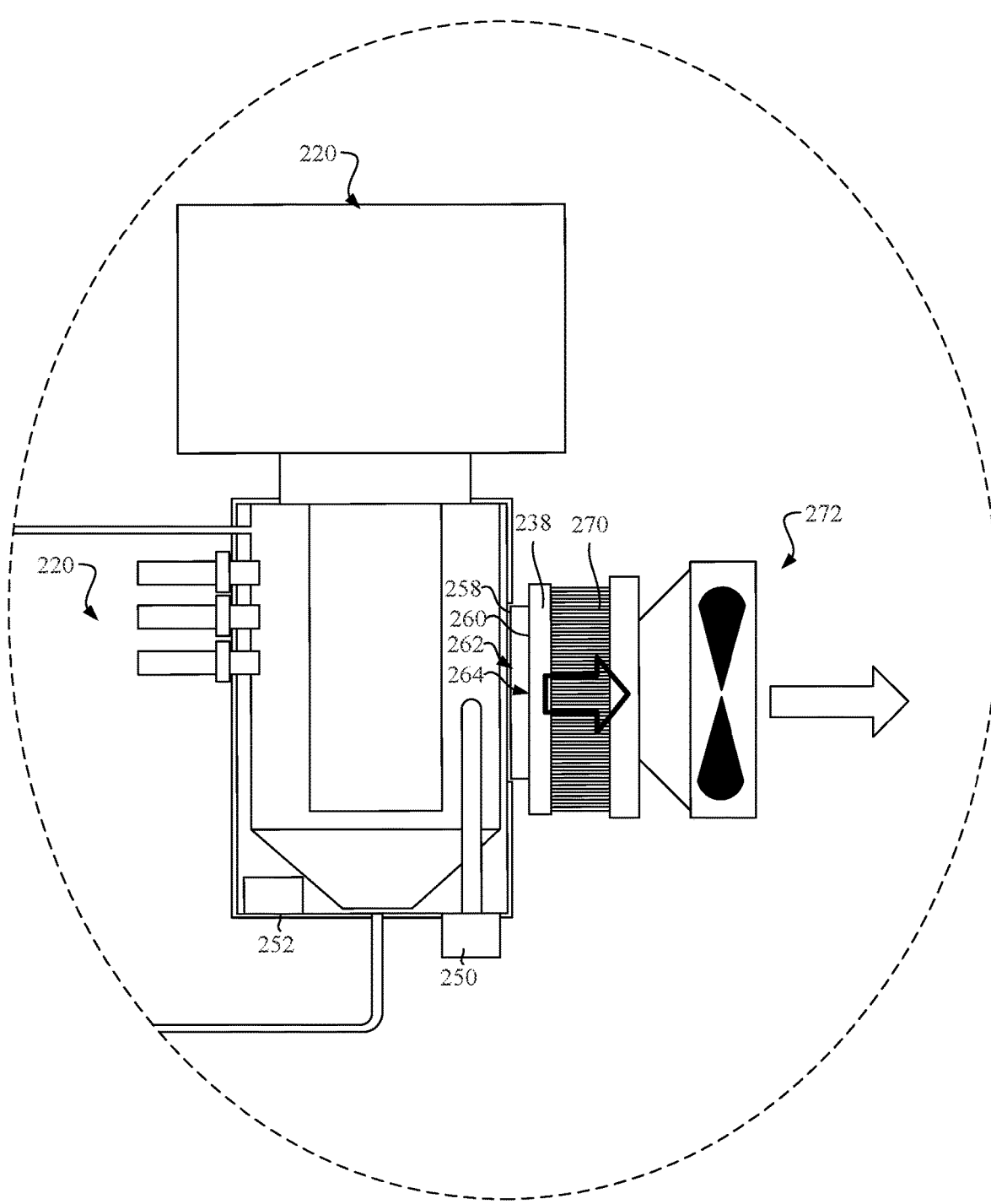
FIG. 3 depicts a detailed view of a fluid chamber of the fluid testing apparatus in accordance with the present disclosure.

FIGS. 2 and 3 depict a schematic of an example of internal components of a fluid testing apparatus 100 in accordance with the present disclosure. FIG. 3 details a portion of the internal components depicted in FIG. 2. In this example, the fluid testing apparatus 100 includes a bottle receiver 106, a pump 200, a fluid conduit 204, a density sensor 216 connected to the fluid conduit 204, a fluid chamber 218, and a rheology sensor 220 connected to the fluid chamber 218.

The bottle receiver 106 may be any appropriate attachment to the exterior of the fluid testing apparatus 100 to which the bottle 108 may be connected and which includes a mechanism for removing the drilling fluid sample 230 from the bottle 108. In the depicted example, a portion of the fluid conduit 204 is suspended from the bottle receiver 106 at a distance so that the inlet 206 is submerged within the drilling fluid sample 230 when the bottle 108 is attached. A filter 202 is connected to the drilling fluid conduit 204 and surrounds the inlet 206 so that solid particles and/or unwanted debris is prevented from entering the fluid conduit 204.

A first portion 210 of the fluid conduit 204 connects the inlet 206 to a pump 200. The pump 200 may be used to pull at least a portion of the drilling fluid sample 230 from the bottle 108 into fluid conduit 204. In some examples, the pump 200 is a peristaltic pump. But, any appropriate type of pump may be used in accordance with the principles described in the present disclosure.

A second portion 212 of the fluid conduit 204 may connect the fluid conduit 204 to the pump 200 and a density sensor. In some cases, the pump 200 is at a higher elevation than the density sensor 216. In this type of example, the pump 200 may release the drilling fluid sample 230 and allow gravity to push the drilling fluid sample 230 to the density sensor 216. In other examples, the pump 200 may actively push the drilling fluid sample 230 through the density sensor 216.

Any appropriate type of density sensor 216 may be used. In one example, the density sensor 216 may be a coriolis density meter that measures a characteristic of the drilling fluid sample 230 as the fluid passes through it. Coriolis density meters may measure the movement/vibrations of internal components of the density meter. These movements may be measured as the drilling fluid sample 230 passes through the density sensor 216. This frequency correlates to the drilling fluid sample's density.

A third portion 214 of the fluid conduit 204 connects the fluid conduit 204 from the density sensor 216 to a fluid chamber 218. The fluid chamber 218 may include a chamber wall 236 that defines an opening 242. An outlet 208 of the fluid chamber 218 may terminate in the opening 242 of the fluid chamber 218 and direct the drilling fluid sample 230 into the fluid chamber 218.

A level detection sensor 222 may send a signal to the pump 200 to stop pumping in the drilling fluid sample 230 when the fluid level 232 is at an appropriate height. Any appropriate type of level detection sensor 222 may be used. A non-exhaustive list of level detection sensors that may be used include ultrasonic sensors, fluid conductivity sensors, capacitance sensors, induction sensors, microwave sensors, laser sensors, float switches, thermal flow switches, hydrostatic pressure sensors, radar based sensors, magnetostrictive sensors, optical sensors, load cell sensors, other types of sensors, time of flight sensors, other types of sensors, or combinations thereof.

While each of the above level detection sensors may be used in some applications, many some of the above mentioned level detection sensors may not be as effective as other types of sensors for certain types of drilling fluids. In some examples, a thermal dispersion level detection sensor is incorporated into the fluid chamber 218 and may be effective for a wide variety of different types of drilling fluids. The thermal dispersion level detection sensor can be effective for determining the level of fluids regardless of the fluid's di-electric strength, tendency to create optical disturbances, and other characteristics of drilling fluids that make level detection challenging.

Thermal dispersion technology is generally used to measure characteristics of a fluid's flow rate. Generally, fluids are cooler when flowing than when in a static condition. Conventionally, thermal dispersion technology analyzes the temperature of a fluid to determine the flow rate or another characteristic of the fluid. In examples where thermal dispersion technology is used in the fluid testing apparatus 100, thermal dispersion technology can be repurposed to determine a fluid level 232.

Level detection with thermal dispersion technology may be accomplished by actively moving the drilling fluid sample 230 as it enters into the fluid chamber 218 and measuring temperature differences at various heights along the fluid chamber 218. In some examples, a rotor 248 may cause the drilling fluid sample 230 to rotate within the fluid chamber 218 as it fills. The rotation of the drilling fluid sample 230 caused by the rotor 248 may create a cooling effect on the portions of the chamber wall 236 in direct contact with the fluid. A fluid level 232 may be determined by comparing the temperature differences along the fluid chamber's wall and identifying the fluid level 232 at the height were the temperature difference occurs.

In the example of FIGS. 2 and 3, the level detection sensor 222 includes a first level detector 224, a second level detector 226, and a third level detector 228. In some cases, each of the first level detector 224, second level detector 226, and third level detector 228 are thermal dispersion level detectors. In other examples, at least one of these detectors is a different type of sensor. For those level detectors that are thermal level detectors, each may include two or more level thermometers that detect the temperature of the chamber wall 236, the temperature adjacent to the exterior of the chamber wall 236, the temperature adjacent to the interior of the chamber wall 236, or combinations thereof. Each of the level thermometers of the level detector may be at adjacent each other, but at different heights. When the lower of the two thermometers is a different temperature than the higher thermometer, the level detector may send signal to stop the pump 200. This temperature difference may indicate that the fluid level 232 is between the lower and higher thermometers.

The second level detector 226 may be used as a back-up if the first level detector 224 fails to operate properly. In this situation, the second level detector 226 may cause a signal to be sent to stop the pump 200.

The third level detector 228 may be used to indicate the fluid level 232 is too high. In some examples, a rheology sensor 220 or other components of the fluid testing apparatus 100 are incorporated into the fluid chamber 218 above the operating fluid level 234. If the fluid level 232 gets too high, the drilling fluid sample 230 may get into these components and interfere with their operation. In one such example, a rotary bearing of a viscometer may be above the operating fluid level 234 in the fluid chamber 218 and if the fluid level 232 exceeds the fluid operating level, the drilling fluid sample 230 may get into the rotary bearings. In some cases, the viscometer's rotary bearings are finely tuned to obtain precise measurement readings. Drilling fluid in these finely tuned bearings may cause the viscometer's measurement outputs to be inaccurate. When activated, the third level detector 228 may cause a message to be communicated to the user that the equipment needs to be checked before proceeding with the tests. In some examples, the third level detector 228 may also send a signal to the stop the pump 200.

In the example of FIGS. 2 and 3, the rheology sensor 220 is a viscometer. The rheology sensor 220 may include a rotor 248 that is suspended into the opening 242 of the fluid chamber 218 to make contact and/or be submerged into the drilling fluid sample 230 when the fluid chamber 218 is filled. In some examples, the rotor 248 is an outer cylinder that rotates about a bob (not shown), which in an inner cylinder. The drilling fluid sample 230 is filled within the annulus between the rotor 248 and the bob. When activated, the rotor 248 rotates at known velocities and creates shear stress on the bob through the drilling fluid sample 230. A torsion spring restrains the movement of the bob and measures the shear stress. The viscometer may run the tests at any appropriate rotor speed (rotations per minute or RPM). In some cases, the tests are taken at 600, 300, 200, 100, 6 and 3 RPM.

An electric temperature controller may be in communication with the fluid chamber 218. Any appropriate type of electric temperature controller may be used in accordance with the principles described in the present disclosure. In some examples, the electric temperature controller includes a thermoelectric material 256 (e.g. Peltier device) that has the characteristic of generating an electric current in response to a temperature differential. The thermoelectric material 256 may include a first side 258 in contact with the outside surface 238 of the fluid chamber 218. In some cases, the thermoelectric material 256 includes a second side 260 that is opposite the first side 258 and is in contact with a heat sink 268.

The thermoelectric material 256 may be part of an electric circuit that can pass an electric current through the thermoelectric material 256 to produce both a heated region 262 and a cooling region 264 within the thermoelectric material 256 simultaneously. A polarity switch may be incorporated into the circuit to change the direction that the electric current passes through the thermoelectric material 256. When the electric current passes through the thermoelectric material 256 in a first direction, the heated region 262 is produced adjacent to the fluid chamber 218 and the cooling region 264 is produced adjacent to the heat sink 268. When the heated region 262 is actively produced adjacent to the fluid chamber 218, the electric temperature controller actively heats the fluid chamber 218. In some cases, when the heated region 262 is produced adjacent to the fluid chamber 218, the fluid chamber's temperature is raised to a higher temperature or the fluid chamber's temperature may be maintained to be at a desired temperature for executing a test on the drilling fluid sample 230. In situations where the electric current passes through the thermoelectric material 256 in a second direction that is opposite of the first direction, the heated region 262 is produced adjacent to the fluid chamber 218 and the heated region 262 is produced adjacent to the heat sink 268. In those situations where the cooling region 264 is actively produced adjacent to the fluid chamber 218, the drilling fluid sample's temperature is lowered to a cooler temperature or the drilling fluid sample's temperature may be maintained to be at a desired temperature for executing a test on the drilling fluid sample 230.

The temperature of the heated region 262 and the cooling region 264 may be controlled with a pulse width modulator. The pulse width modulator may switch the electric circuit on and off at a frequency rate that produces an average current flow. The longer the pulse width modulator causes electric current to flow through the thermoelectric material 256 compared to the periods where the flow of electric current is stopped, the higher the total power supplied to the thermoelectric material 256 resulting in a higher temperature being produced in the heated region 262 and a lower temperature in the cooling region 264. The difference in temperatures between the heated region 262 and the cooling region 264 may be lowered by increasing the periods of time that the electric current is stopped from flowing through the thermoelectric material 256. The pulse width modulator may cause the thermoelectric material 256 to adjustably heat or cool the fluid chamber 218 to each of the desired temperatures for each of the tests that are to be performed with the fluid chamber 218.

The fluid chamber 218 may be made of a thermally conductive material that spreads the temperature produced by first side 258 of the thermoelectric material 256. In this embodiments, the fluid chamber 218 is made of aluminum, but the fluid chamber 218 may be made of other types of thermally conductive materials. A non-exhaustive list of thermally conductive materials that may be used to make the fluid chamber 218 include aluminum, copper, gold, magnesium, beryllium, tungsten, other metals, mixtures thereof, alloys thereof, or combinations thereof. In some cases, the fluid chamber 218 is entirely made of a material that has a substantially consistent thermal conductivity. In other examples, the inside surface of the chamber wall 236 is lined with a material with a different thermal conductivity than other materials that makes up a different portion of the fluid chamber 218.

The contact surface 240 of the outside surface 238 of the fluid chamber 218 that is adjacent to the thermoelectric material 256 may include a smooth surface roughness that is in thermal contact with the thermoelectric material 256. In some examples, the contact surface 240 includes a polished surface. Further, in some embodiments, the contact surface 240 includes a smoother finish that other portions of the outside surface 238 of the fluid chamber 218. The smooth finish of the contact surface 240 may reduce gaps between the thermoelectric material 256 and the outside surface 238 of the fluid chamber 218. In some examples, a thermally conductive paste may be used to fill the gaps between the contact surface 240 and the thermoelectric material 256. Even in examples where the contact surface 240 has a smooth finish, the contact surface 240 may still have small gaps that can minimize the thermal transfer between the thermoelectric material 256 and the fluid chamber 218 and the thermally conductive paste may be used in these examples to increase the thermal transfer.

The outside surface 238 of the fluid chamber 218 may be at least partially surrounded with an insulation layer 244. The insulation layer 244 may minimize ambient conditions that would otherwise heat or cool the fluid chamber 218. For example, the insulation layer 244 may prevent an ambient temperature outside of the fluid chamber 218 from heating or cooling the fluid chamber 218 away from the desired temperature for executing a rheology test. In some cases, the insulation layer 244 may prevent the formation of condensation on the outside of the fluid chamber 218, which can cause unwanted cooling of the fluid chamber 218 when bringing the drilling fluid sample 230 to a higher temperature or trying to maintain the drilling fluid sample 230 at a higher temperature.

The fluid chamber 218 may include at least one fluid thermometer 250 that measures the temperature of the drilling fluid sample 230. The fluid chamber 218 may also include at least one equipment thermometer 252 that may measure the temperature of at least one piece of equipment associated with the drilling fluid sample 230. For example, the equipment thermometer 252 may measure the temperature of the material forming the fluid chamber 218. Temperature measurements of the fluid chamber's material may prevent overheating of the fluid chamber 218.

The heat sink 268 may be made of a thermally conductive material and include fins 270 that increase the surface area of the heat sink 268. The fins 270 can be used to exchange temperature with a fluid medium, such as air or a liquid. In examples where the heated region 262 is produced on the second side 260, the heat generated by the heated region 262 can spread throughout the heat sink 268 and be transferred through the fins 270 into the fluid medium. In some cases, a fan 272 is positioned adjacent to the heat sink 268 to cause air to flow through the fins 270 to increase the rate at which the heat is dissipated into the air. In other examples, a water or another type of liquid may be passed over the fins 270 as the fluid medium. In this example, the liquid medium does not make contact with the fluid chamber 218, but instead makes contact with the fins 270 of the heat sink 268.

Figure 4:
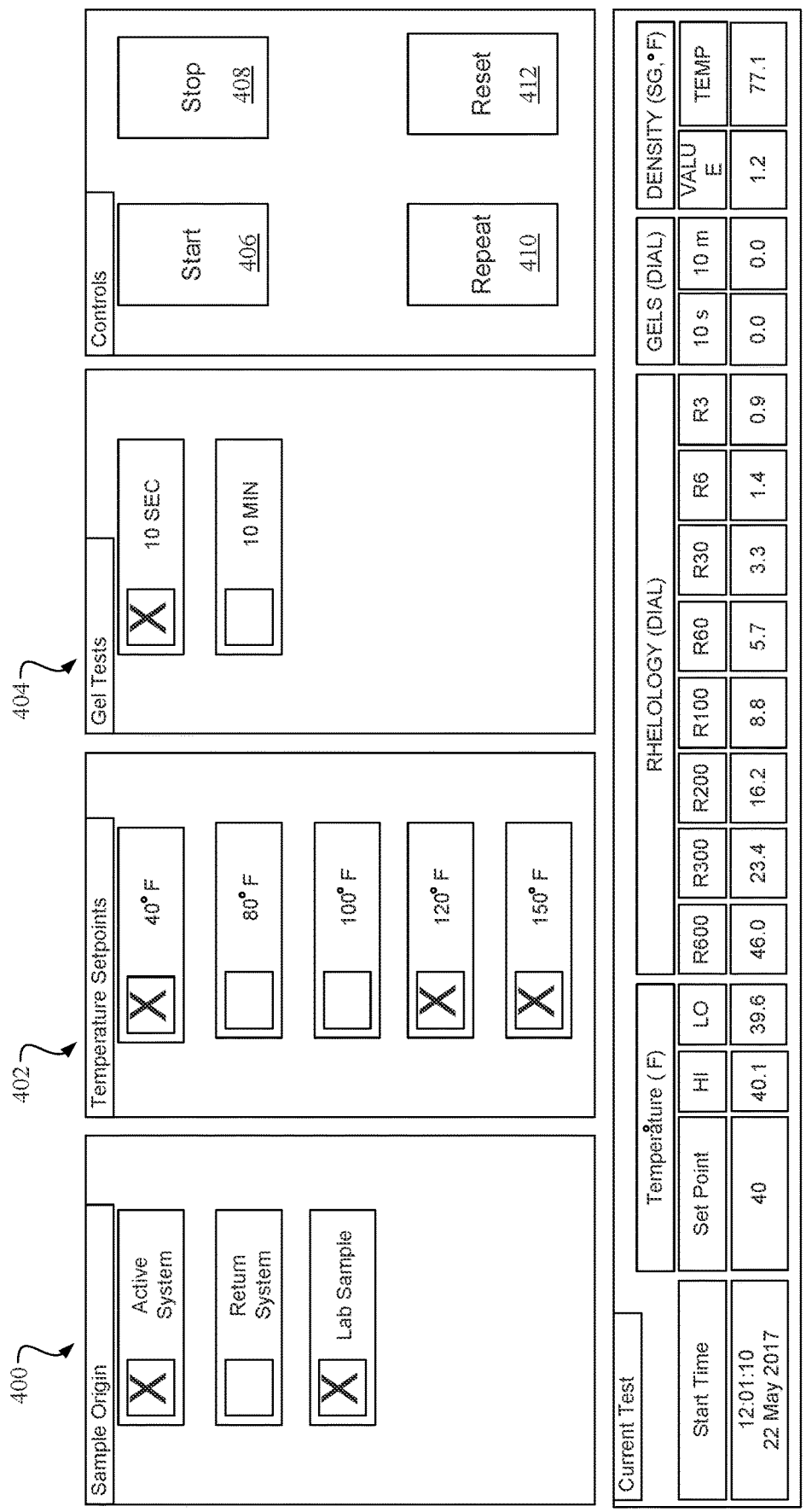
FIG. 4 depicts an example of a user interface of the fluid testing apparatus in accordance with the present disclosure.

FIG. 4 depicts an example of a user interface 104 of the fluid testing apparatus 100 in accordance with the present disclosure. In this example, the user interface 104 presents a format for the user to instruct the fluid testing apparatus 100 about performing the tests. In this example, the format includes sample origin options 400 to select the origin of drilling fluid sample 230, temperature set point options 402 for each of the tests, and duration options 404 for each of the tests. Additionally, the user interface 104 presents controls for sending instructions to the fluid testing apparatus 100.

In this example, the user is provided with five temperature set point for performing tests. While the illustrated example depicts five different temperatures for conducting the tests, any appropriate temperature values may be presented to the user as well as any appropriate number of temperature set point options may be presented.

In the depicted example, the test durations are depicted as a ten second option or a ten minute option. But, any appropriate test duration may be presented in accordance with the principles disclosed herein. Further, any appropriate number of test duration options 404 may be presented through the user interface 104.

While the example of FIG. 4 depicts the format presenting a limited number of options that the user can select, in other examples the format presents open fields where the user may specify the values for temperature, test durations, or other testing parameters. Also, some examples may provide the user an ability to add any number of tests to the executed by the fluid testing apparatus 100.

The controls provided in the depicted example include a start command 406, a stop command 408, a repeat command 410, and a reset command 412. The start command 406 may be selected by the user when he or she desires to start the tests. In some examples, in response to sending the start command 406, the fluid testing apparatus 100 executes each of the tests in a sequence without having to have additional involvement from the user. In some examples, the testing sequence includes performing the first test at the lowest selected temperature set point and performing the second test at the second lowest selected temperature set point and so forth until final test is performed at the highest selected temperature set point.

Figure 5:
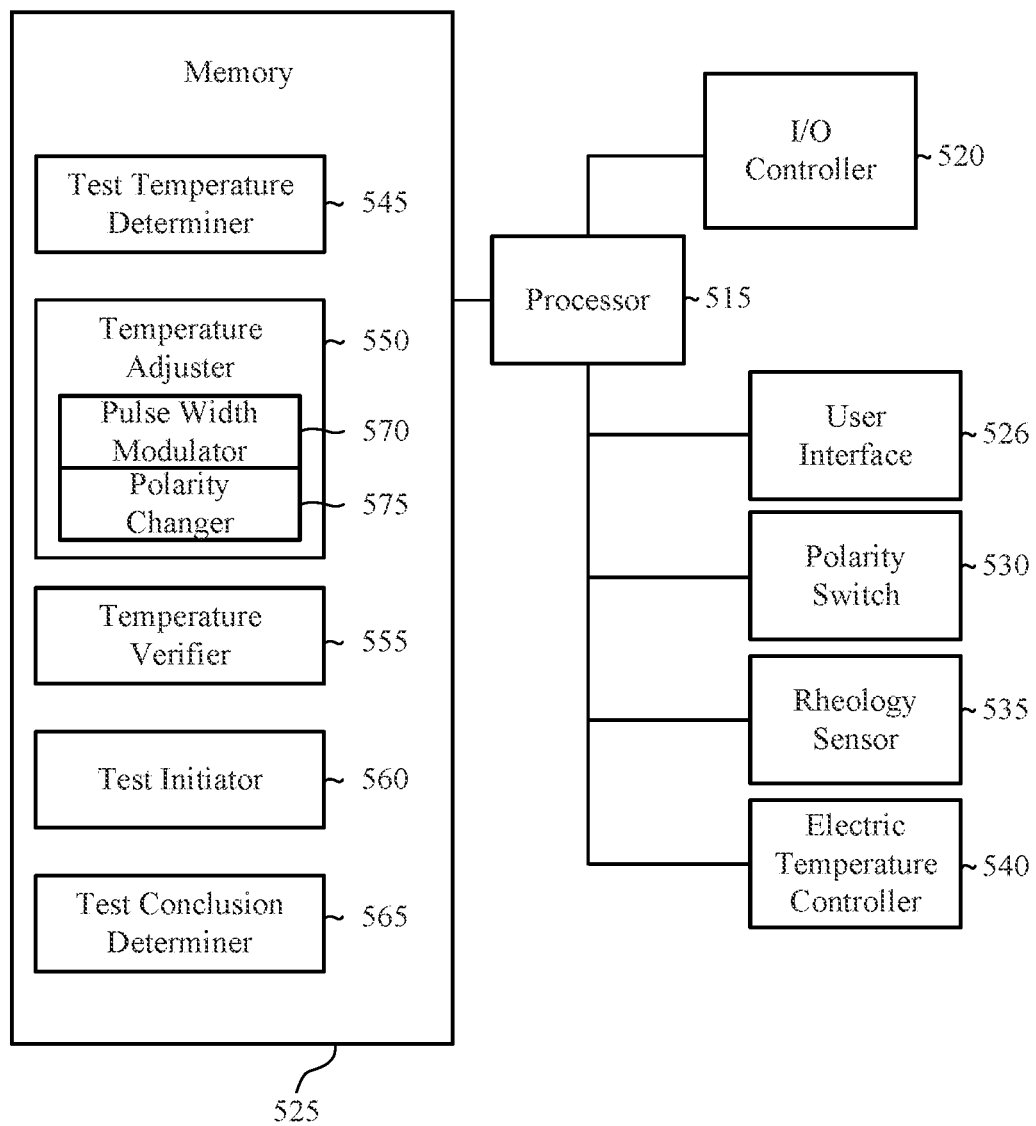
FIG. 5 depicts a diagram of a system for adjusting a temperature of fluid samples in accordance with the present disclosure.

FIG. 5 depicts a diagram of a system 500 for testing drilling fluid samples. The system 500 includes a processor 515, an I/O controller 520, memory 525, a user interface 526, a polarity switch 530, a rheology sensor 535, and an electric temperature controller 540. These components may communicate wirelessly, through hard wired connections, or combinations thereof. The memory 525 of the system may include a test temperature determiner 545, a temperature adjuster 550, a temperature verifier 555, a test initiator 560, and a test conclusion determiner 565. The temperature adjuster 550 includes a pulse width modulator 570, and a polarity changer 575.

The processor 515 may include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some cases, the processor 515 may be configured to operate a memory array using a memory controller. In other cases, a memory controller may be integrated into the processor 515. The processor 515 may be configured to execute computer-readable instructions stored in a memory to perform various functions (e.g., functions or tasks supporting the evaluation of prescribed optical devices).

The I/O controller 520 may represent or interact with a modem, a keyboard, a mouse, a touchscreen, or a similar device. In some cases, the I/O controller 520 may be implemented as part of the processor. In some cases, a user may interact with the system via the I/O controller 520 or via hardware components controlled by the I/O controller 520. The I/O controller 520 may be in communication with any appropriate input and any appropriate output.

The memory 525 may include random access memory (RAM) and read only memory (ROM). The memory 525 may store computer-readable, computer-executable software including instructions that, when executed, cause the processor to perform various functions described herein. In some cases, the memory 525 may contain, among other things, a basic input/output system (BIOS) which may control basic hardware and/or software operation such as the interaction with peripheral components or devices.

The test temperature determiner 545 represents programmed instructions that cause the processor 515 to determine the temperature at which a test is to be performed. In some examples, the test temperature is determined by accessing information the user inputted into the user interface.

The temperature adjuster 550 represents programmed instructions that cause the processor 515 to adjust the temperature of the drilling fluid sample. Part of the process of adjusting the temperature may include determining the current temperature of the drilling fluid sample and determining whether the desired temperature for the next test is higher or lower than the current temperature of the drilling fluid sample. Based on whether the temperature of the drilling fluid sample is to be increased or decreased, the polarity changer 575 may cause the processor 515 to send an instruction to the polarity switch 530 to direct electric current through the thermoelectric material in the appropriate direction. The pulse width modulator 570 may send an instruction to the electric temperature controller 540 to adjust the strength of the electric current to run through the thermoelectric material. When the temperature of the drilling fluid sample is being actively changed, the pulse width modulator 570 may cause the signal strength to be greater than when the signal strength is intended to just maintain the drilling fluid sample at its current temperature for testing.

The temperature verifier 555 represents programmed instructions that cause the processor 515 to determine the current temperature of the drilling fluid sample. This information can be consulted by the temperature adjuster 550 to determine when to change the signal strength from actively changing the temperature of the drilling fluid sample to maintaining the temperature of the drilling fluid sample.

The test initiator 560 represents programmed instructions that cause the processor 515 to cause the test to be performed with the rheology sensor 535. The test initiator 560 may also consult information from the temperature verifier 555 to determine if the drilling fluid sample is at the appropriate temperature for executing the test.

The test conclusion determiner 565 represents programmed instructions that cause the processor 515 to determine when a test is completed. In some examples, the test conclusion determiner 565 sends a signal to the temperature adjuster at the conclusion of a test at a first temperature. In response, the temperature adjuster 550 may start the process for changing the temperature of the drilling fluid sample for the next test at a different desired temperature.

Figure 6:
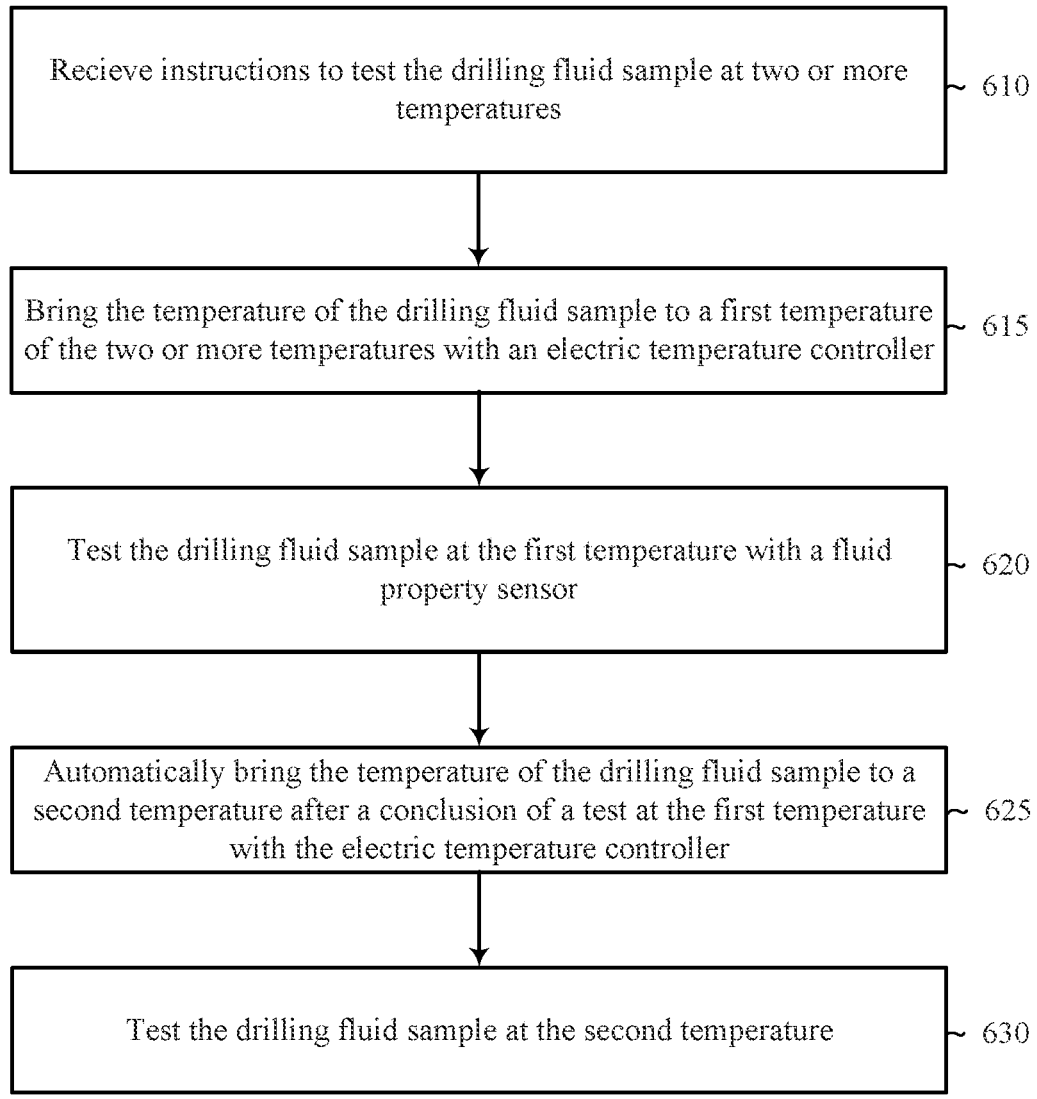
FIG. 6 depicts an example of a method for automated testing of the fluid samples at different temperatures in accordance with the present disclosure.

FIG. 6 depicts an example of a method 600 for automated testing of the fluid samples at different temperatures in accordance with the present disclosure. In this example, the method 600 includes supplying a drilling fluid sample into a fluid chamber, receiving 610 instructions to test the drilling fluid sample at two or more temperatures, bringing 615 the temperature of the drilling fluid sample to a first temperature of the two or more temperatures through the fluid chamber with an electric temperature controller, testing 620 the drilling fluid sample at the first temperature with a rheology sensor incorporated into the fluid chamber, automatically bringing 625 the temperature of the drilling fluid sample to a second temperature after a conclusion of a test at the first temperature with the electric temperature controller, and testing 630 the drilling fluid sample at the second temperature with the rheology sensor. At least some of the portions of this method may be carried out in accordance with the principles described in the present disclosure.

Figure 7:
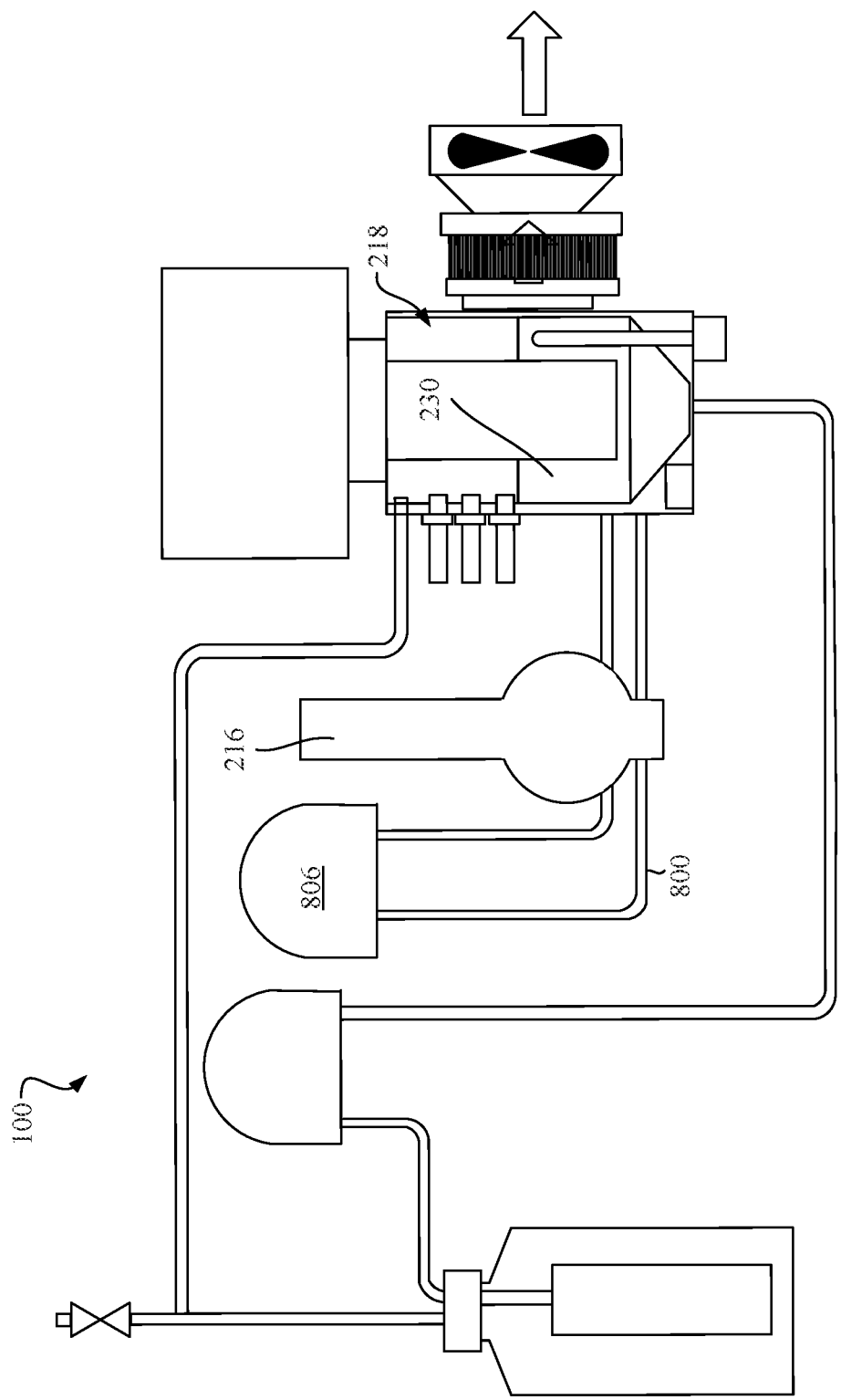
FIG. 7 depicts an example of components of a fluid testing apparatus with a side loop for controlling a temperature of fluid for density measurements in accordance with the present disclosure.

FIG. 7 depicts an example of components of a fluid testing apparatus 100 with a side loop 800 for controlling a temperature of fluid for density measurements in accordance with the present disclosure. In the depicted example, a side loop 800 is incorporated into the fluid testing apparatus 100. A second pump 806 and the density sensor 216 is incorporated into the side loop 800. The second pump 806 may cause a portion of the drilling fluid sample 230 to enter into the side loop 800 from the fluid chamber 218 when the drilling fluid is at a desired temperature for testing the density of the drilling fluid sample 230.

Figure 8:
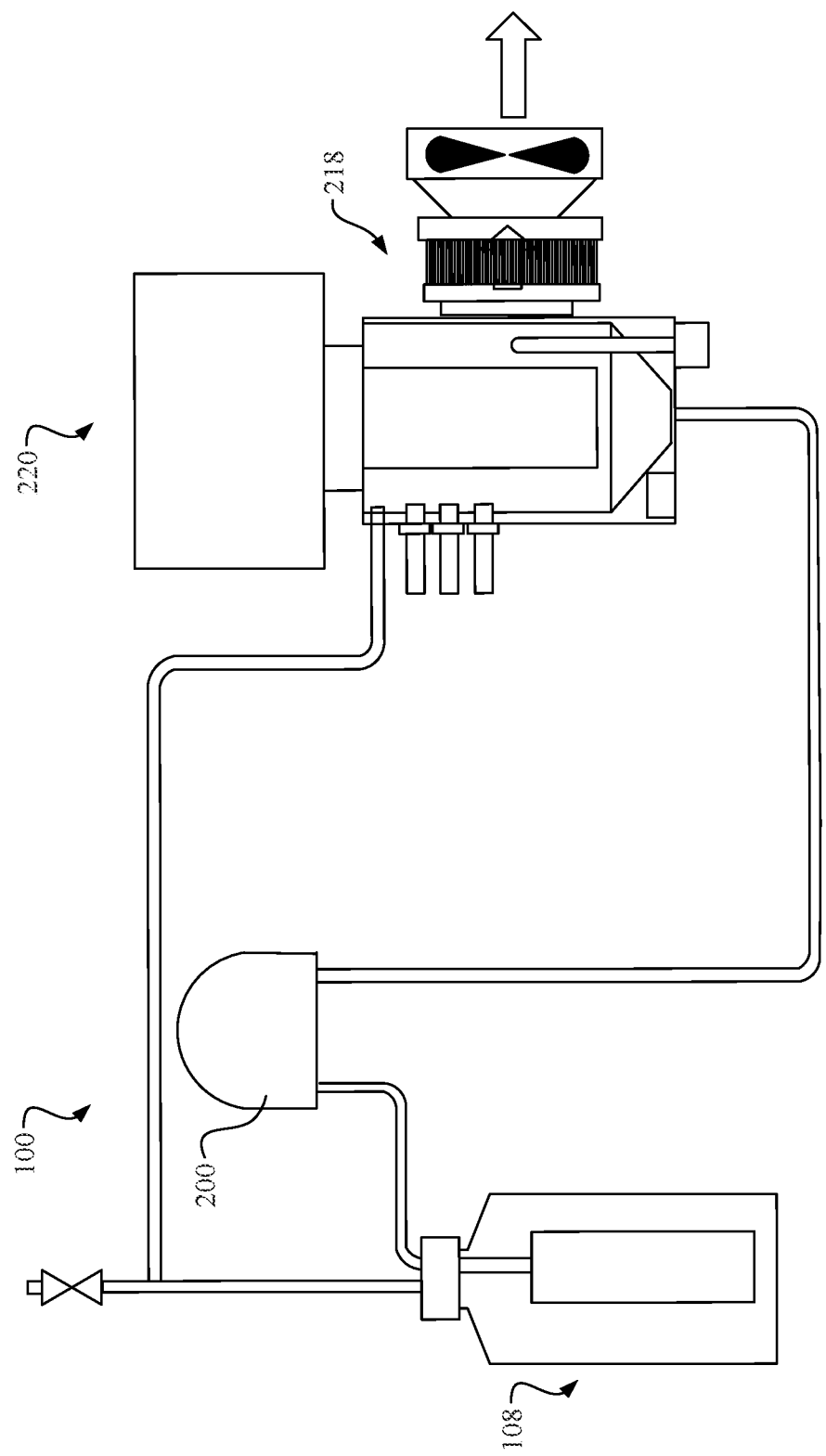
FIG. 8 depicts an example of components of a fluid testing apparatus without a density sensor in accordance with the present disclosure.

In some examples, the user interface presents the user with options to test the rheology of the drilling fluid sample 230, to test the density of the drilling fluid sample 230, or combinations thereof. The user may instruct the fluid testing apparatus 100 to test the drilling fluid at the same temperature at which the rheology sensor 220 tests the drilling fluid sample 230. In other examples, the density of the drilling fluid sample 230 may be tested at a temperature that is different from at least one of the tests conducted with the rheology sensor 220. In some cases, the electric heating controller brings the drilling fluid sample 230 to a temperature for tests performed by either the rheology sensor 220, the density sensor 216, another type of sensor incorporated into the fluid chamber 218, or combinations thereof. In the example of FIG. 8, the fluid testing apparatus 100 does not include a density sensor 216 in accordance with the present disclosure.

While the fluid testing apparatus has been described above as having a bottle receiver for connection to a bottle containing the drilling fluid sample, in some examples, no bottle receiver is incorporated into the fluid testing apparatus. For example, the user may pour the drilling fluid sample into a tank incorporated into the fluid testing apparatus. In some examples where the drilling fluid sample is incorporated into the fluid testing apparatus, a filter may be incorporated into an outlet of the tank to filter out sand, debris, other types of solids, or combinations thereof. In some cases, the user may pour the drilling fluid sample directly into the fluid chamber connected to the viscometer or other rheology sensor.

In one embodiment, a system includes a fluid conduit, a fluid chamber in communication with the fluid conduit, a rheology sensor in communication with the fluid chamber, and an electric temperature controller in communication with the fluid chamber. The fluid chamber is cooled in response to a first control signal from the electric temperature controller.

A method includes receiving instructions to test a drilling fluid sample at two or more temperatures, bringing a temperature of the drilling fluid sample to a first temperature of the two or more temperatures with an electric temperature controller, testing the drilling fluid sample at the first temperature with a fluid property sensor, automatically bringing the temperature of the drilling fluid sample to a second temperature after a conclusion of a test at the first temperature with the electric temperature controller, and testing the drilling fluid sample at the second temperature.

An apparatus includes a fluid chamber where the fluid chamber includes a chamber wall and an opening defined by the chamber wall. The apparatus also includes a rheology sensor in communication with the fluid chamber. The rheology sensor includes a rotor protruding into the opening where the rotor is supported at a depth within the opening to contact a fluid sample when the fluid chamber is filled with a fluid to an operating level. Further, the apparatus includes at least one thermal dispersion sensor that detects a level of the fluid sample when the rotor causes the fluid sample to move within the fluid chamber and an electric temperature controller in communication with the fluid chamber that is configured to control a temperature of the fluid sample within the fluid chamber.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A system, comprising:
   a fluid conduit;
   a fluid chamber in communication with the fluid conduit to enable the fluid chamber to receive a fluid from the fluid conduit;
   a rheology sensor in communication with the fluid chamber to enable the rheology sensor to test a rheological parameter of the fluid while the fluid is in the fluid chamber;
   a density sensor positioned along a side loop extending from the fluid chamber to enable the density sensor to test a density of a portion of the fluid extracted from the fluid chamber, wherein the side loop comprises a fluid inlet connected to a first portion of the fluid chamber and a fluid outlet connected to a second portion of the fluid chamber;
   an electric temperature controller in communication with the fluid chamber, wherein the fluid chamber is cooled in response to a first control signal from the electric temperature controller, wherein the electric temperature controller includes a thermoelectric material that produces a heated region and a cooling region, and wherein the electric temperature controller includes a pulse width modulator to switch electric current to the thermoelectric material on and off;
   a processor; and
   memory in communication with the processor, wherein the memory stores instructions that cause the processor to:
      receive a user input of a first desired temperature for testing the density of the fluid; and
      provide a control signal to operate a pump to cause the portion of the fluid to enter the side loop when the fluid within the fluid chamber is at the first desired temperature to enable the density sensor to test the density of the portion of the fluid at the first desired temperature, wherein the first desired temperature is different from a second desired temperature at which the rheology sensor tests the rheological parameter of the fluid while the fluid is in the fluid chamber.

2. The system of claim 1, wherein the fluid chamber is heated in response to a second control signal from the electric temperature controller.

3. The system of claim 2, wherein the second control signal has an opposite polarity than the first control signal.

4. The system of claim 1, wherein the electric temperature controller includes a heat sink in communication with the thermoelectric material.

5. The system of claim 1, further comprising:
   a polarity switch in communication with the thermoelectric material,
   wherein when the polarity switch directs electricity in a first direction through the thermoelectric material, the heated region is produced on a first side of the thermoelectric material and the cooling region is produced on a second side of the thermoelectric material, and
   wherein when the polarity switch directs electricity in a second direction, opposite to the first direction, through the thermoelectric material, the heated region is produced on the second side of the thermoelectric material and the cooling region is produced on the first side of the thermoelectric material.

6. The system of claim 1,
   wherein the instructions that cause the processor to:
      receive an additional user input to test a fluid sample of the fluid in the fluid chamber with the rheology sensor at two or more different temperatures comprising the second desired temperature and a third desired temperature;
      with the electric temperature controller, bring a temperature of the fluid sample to the second desired temperature of the two or more different temperatures;
      test the fluid sample with the rheology sensor at the second desired temperature;
      automatically, with the electric temperature controller, bring the temperature of the fluid sample to the third desired temperature of the two or more different temperatures; and
      test the fluid sample with the rheology sensor at the third desired temperature.

7. The system of claim 1, further including at least one level detection sensor incorporated into the fluid chamber.

8. The system of claim 7, wherein the at least one level detection sensor is a thermal dispersion sensor.

9. The system of claim 1, further including an insulation layer covering an outside surface of the fluid chamber.

10. The system of claim 1, wherein the thermoelectric material contacts a polished surface of the fluid chamber.

11. The system of claim 1,
wherein the instructions cause the processor to:
with the electric temperature controller, bring the temperature of the fluid in the fluid chamber to the first desired temperature; and
provide the control signal to operate the pump to cause the portion of the fluid to enter the side loop when the fluid within the fluid chamber is at the first desired temperature to thereby control a temperature of the portion of the fluid to correspond to the first desired temperature during the test of the density of the portion of the fluid.

12. The system of claim 1, further comprising:
a rotor positioned in the fluid chamber; and
at least one level detection sensor comprising a thermal dispersion sensor,
wherein the instructions cause the processor to:
instruct rotation of the rotor in the fluid chamber as the fluid flows into the fluid chamber;
receive inputs from the thermal dispersion sensor during the rotation of the rotor as the fluid flows into the fluid chamber; and
block flow of the fluid from the fluid conduit into the fluid chamber in response to determining, based on the inputs, that a level of the fluid within the fluid chamber matches an operating level.

13. A method, comprising:
receiving instructions to test a drilling fluid sample at two or more temperatures;
instructing rotation of a rotor positioned within a fluid chamber as drilling fluid flows into the fluid chamber;
receiving inputs from a thermal dispersion sensor during the rotation of the rotor as the drilling fluid flows into the fluid chamber;
blocking flow of the drilling fluid into the fluid chamber to provide the drilling fluid sample within the fluid chamber in response to determining, based on the inputs, that a level of the drilling fluid within the fluid chamber matches an operating level;
bringing a temperature of the drilling fluid sample in the fluid chamber to a first temperature of the two or more temperatures using an electric temperature controller with current adjusted using a pulse width modulator;
testing the drilling fluid sample at the first temperature using a fluid property sensor coupled with the electric temperature controller;
automatically bringing the temperature of the drilling fluid sample in the fluid chamber to a second temperature after a conclusion of a test at the first temperature using the electric temperature controller by adjusting current to the electric temperature controller using the pulse width modulator; and
testing the drilling fluid sample at the second temperature.

14. The method of claim 13, wherein bringing the temperature of the drilling fluid sample to the first temperature or the second temperature includes applying a current set by the pulse width modulator to a thermoelectric material in thermal contact with the drilling fluid sample.

15. The method of claim 13, further comprising:
extracting a portion of the drilling fluid sample through a side conduit extending from the fluid chamber; and
measuring a density of the portion of the drilling fluid sample with a density sensor positioned along the side conduit extending from the fluid chamber.

16. An apparatus, comprising:
a fluid chamber, the fluid chamber including:
a chamber wall; and
an opening defined by the chamber wall;
a rheology sensor in communication with the fluid chamber, the rheology sensor further including a rotor protruding into the opening;
at least one thermal dispersion sensor disposed through a side of the fluid chamber, wherein the at least one thermal dispersion sensor detects a level of a fluid sample in the fluid chamber while the rotor rotates as fluid flows into the fluid chamber to cause the fluid sample to move within the fluid chamber;
a processor and memory in communication with the processor, wherein the memory stores instructions to cause the processor to stop flow of the fluid into the fluid chamber in response to determining, based on inputs from the at least one thermal dispersion sensor, that the level of the fluid sample within the fluid chamber matches an operating level; and
an electric temperature controller in communication with the fluid chamber that is configured to control a temperature of the fluid sample within the fluid chamber.

17. The apparatus of claim 16, wherein the electric temperature controller further includes:
a thermoelectric material;
a first side of the thermoelectric material being in contact with an outside surface of the fluid chamber; and
a second side of the thermoelectric material being in contact with a heat sink.

18. The apparatus of claim 17, wherein the thermoelectric material has a characteristic of:
producing a heated region adjacent to the fluid chamber and a producing a cooling region adjacent to the heat sink in response to a first control signal applied across the thermoelectric material; and
producing the heated region adjacent to the heat sink and a producing the cooling region adjacent to the fluid chamber in response to a second control signal applied across the thermoelectric material when the second control signal has an opposite polarity to the first control signal.

19. The apparatus of claim 17, further comprising:
a processor;
memory in communication with the processor, wherein the memory stores instructions that cause the processor to:
receive input to test the fluid sample in the fluid chamber with the rheology sensor at multiple temperatures;
automatically bring and maintain the temperature of the fluid sample to each of the multiple temperatures; and
automatically test the fluid sample with the rheology sensor at each of the multiple temperatures.

20. The apparatus of claim 17, further comprising a pulse width modulator to switch electric current to the thermoelectric material on and off.

* * * * *